US00PP32365P2

(12) United States Plant Patent
Meyer

(10) Patent No.: US PP32,365 P2
(45) Date of Patent: Oct. 20, 2020

(54) ***HEMEROCALLIS* PLANT NAMED 'HUNGRY EYES'**

(50) Latin Name: ***Hemerocallis* (L.) hybrid**
Varietal Denomination: Hungry Eyes

(71) Applicant: Chris Meyer, Zeeland, MI (US)

(72) Inventor: Chris Meyer, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/873,090

(22) Filed: Jan. 30, 2020

(51) Int. Cl.
*A01H 5/02* (2018.01)
*A01H 6/00* (2018.01)

(52) U.S. Cl.
USPC ..... Plt./312
CPC ..... *A01H 6/00* (2018.05)

(58) Field of Classification Search
USPC ..... Plt./312
CPC ..... A01H 6/00
See application file for complete search history.

*Primary Examiner* — Anne Marie Grunberg

(57) ABSTRACT

A new and distinct *Hemerocallis* plant named 'Hungry Eyes' characterized by winter-hardy compact habit with clean medium-green foliage that goes dormant in the winter. The flowers are rounded, fragrant, single, mauve-pink with a tint of orange, with a wide wine reddish-purple eye band and matching picotee edge and yellow throat. Tepals are slightly reflexed near apices with the outer tepal set having consistent, considerable, wine reddish-purple crisped margins. The new plant flowers on stems up to 56 cm tall with four-way branching beginning about mid-July and repeating late into summer.

1 Drawing Sheet

Botanical classification: *Hemerocallis* (L.) hybrid.
Variety denomination: 'Hungry Eyes'.

STATEMENT REGARDING PRIOR DISCLOSURES UNDER 37 CFR 1.77(B)(6)

The first non-enabling disclosure was the brief description and photograph on a website maintained by Walters Gardens, Inc. on Feb. 1, 2019. Subsequently, on May 29, 2019 the new plant was advertised in the "Walters Gardens 19-20 Catalog" followed by a number of sales made by Walters Gardens, Inc. on Jul. 8, 2019. Walters Gardens, Inc. obtained the new plant and all information relating to the new plant, from the inventor. No plants of *Hemerocallis* 'Hungry Eyes' have been sold in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to a new and distinct daylily plant, *Hemerocallis* 'Hungry Eyes' hereinafter also referred to as the new plant or just the cultivar name, 'Hungry Eyes'. *Hemerocallis* 'Hungry Eyes' was hybridized by the inventor, Chris Meyer, in the spring of 2005 in a greenhouse at a wholesale perennial nursery in Zeeland, Mich., USA. The new plant originated from a breeding program conducted by the inventor with the specific intention to improve the garden worthiness, expand color regimens and increase flowering period which were some of the criteria of further trials in the trial beds at the same nursery in Zeeland, Mich. The female or seed parent was 'Bridgeton Gem' (not patented) and the male or pollen parent was 'Johnny Cash' (not patented). The new plant was selected as a single seedling from this cross, and after confidential evaluations in a trial bed beginning in 2008 in Zeeland, Mich. was assigned the breeder code 05-685-8. The new plant has been asexually propagated by division at the same wholesale nursery in Zeeland, Mich. since 2009 with all resultant asexually propagated plants having retained all the same unique traits as the original plant. *Hemerocallis* 'Hungry Eyes' is stable and reproduces true to type in successive generations of asexual reproduction.

There are nearly 90,000 registered daylilies with The American *Hemerocallis* Society, which is the International Cultivar Registration Authority for the genus *Hemerocallis*. In comparison to the new plant, the female parent has a cream flower color with a burgundy eye and picotee margin of the inner tepals, a yellow-green throat. In comparison to the new plant, the male parent has a dark reddish-purple flower with a thin golden picotee margin on the inner tepals and a green throat. 'Johnny Cash' is also taller in flower and flowers earlier in the season.

The most similar daylily known to the inventor are: 'Clarification' (not patented), 'Final Episode' (not patented), 'Frank Sechs' (not patented) 'Sound of My Heart' U.S. Plant patent application Ser. No. 16/602,733 and 'Roy's Picotee' (not patented).

'Clarification' has flowers with narrower tepals that are pinkish-lavender with a dark reddish-purple eye and picotee margin. 'Final Episode' has taller flower stems with larger flowers that more recurved tepals with faintly colored midribs, lighter pink base and lighter red eye and picotee margin. 'Frank Sechs' has larger flowers with a lavender-pink base, a seeping grape-purple eye-zone and narrower grape-purple picotee margin with yellowish-green throat on slightly taller scapes. 'Sound of My Heart' has pastel-pink base with a lighter wine-purple eye and picotee margin and yellowish-green throat. 'Roy's Picotee' has flowers with a lighter ivory-mauve base, narrower less rounded inner tepals and a lighter purple eye zone on slightly taller stems.

*Hemerocallis* 'Hungry Eyes' differs from all other daylilies known to the applicant, by the combination of the following traits:

1. Winter-hardy, compact habit with clean medium-green foliage that goes dormant in the winter;
2. Fragrant, single, limbate, rounded flowers about 13.5 cm across of mauve-rose with a tint of orange, a very wide wine reddish-purple eye zone and matching ruffled picotee edge and yellow throat;
3. Inner and outer tepals with consistent, considerable, wine reddish-purple crisped margins.
4. Tepals slightly reflexed near apices;
5. Plants produce four-way branched scapes of about 56 cm tall with up to 16 flowers per scape;
6. Flowering begins about mid to late-July with excellent coverage and repeat flowering late in the season;

BRIEF DESCRIPTION OF THE DRAWINGS

The photograph of the new plant demonstrates the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
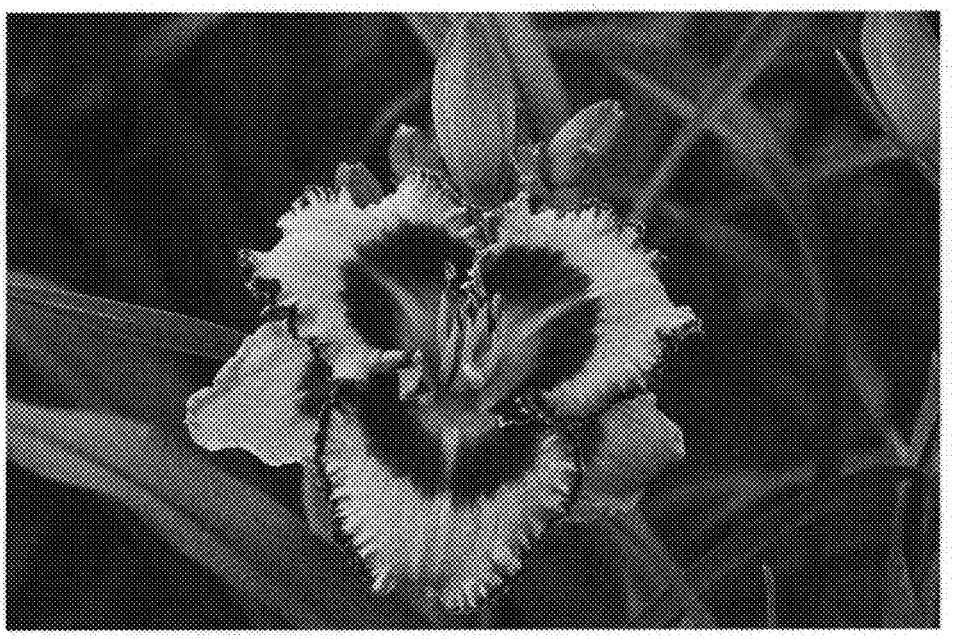
FIG. 1 shows a close-up of a flower and bud.
Figure 2:
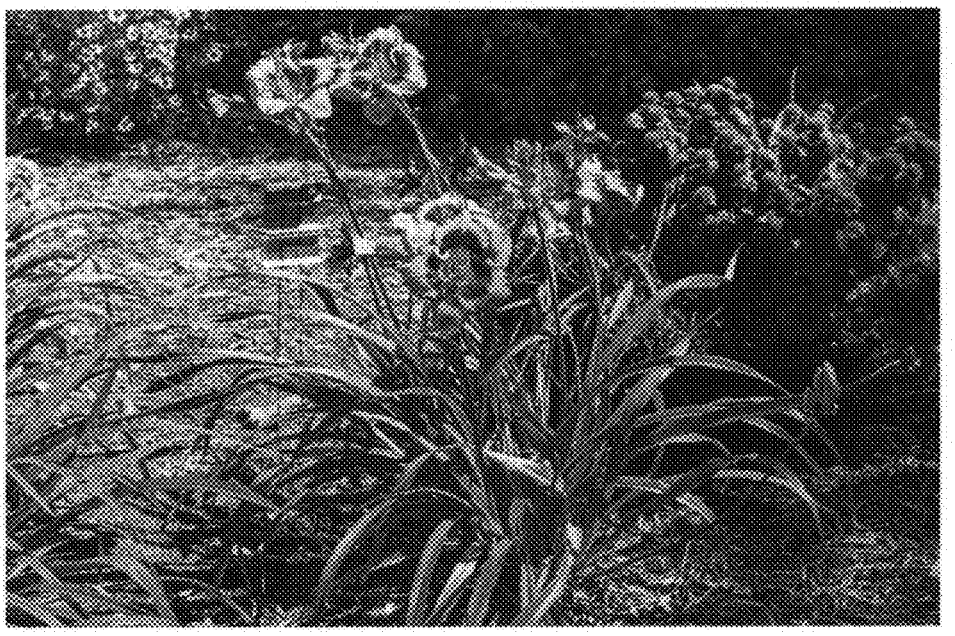
FIG. 2 shows a three-year-old plant in peak flower in a sunny landscape during mid-summer at a display garden in Zeeland, Mich.

The following descriptions and color references are based on the 2015 edition of The Royal Horticultural Society Colour Chart except where common dictionary terms are used. The new plant, *Hemerocallis* 'Hungry Eyes', has not been observed under all possible environments. The phenotype may vary slightly with different environmental conditions, such as temperature, light, fertility, moisture and maturity levels, but without any change in the genotype. The following observations and size descriptions are of a three-year-old plant in a sunny landscape at a display garden in Zeeland, Mich. with and supplemental water and fertilizer.

Botanical classification: *Hemerocallis* (L.) hybrid;

Parentage: Female (seed) parent is 'Bridgeton Gem'; male (pollen) is 'Johnny Cash';

Propagation: Division of the rhizome;

Growth rate: Moderate to rapid;

Crop time: About 8 to 10 weeks to flower starting in spring in a 3.8 liter container from vernalized one-year-old plant;

Rooting habit: Fleshy, about 2.5 mm diameter; lightly branching;

Root color: Nearest RHS 159C depending on soil type;

Plant shape and habit: Winter-hardy herbaceous perennial with four basal shoots emerging from rhizomes producing a radially symmetrical mound of arching leaves;

Plant size: Foliage height about 45.0 cm tall from soil line to the top of the leaves and about 85.0 cm wide at the widest point;

Leaves: Entire, glabrous, slightly glaucous abaxial and adaxial, linear, sessile; folded; apex narrowly acute, base sheathing; to about 63.0 cm long and 25.0 mm across, average about 57.0 cm long and about 23.0 mm across; about 20 leaves per division;

Cauline leaves: 1 to 2 per scape; reduced, average about 3.0 cm long and 9.0 mm across;

Leaf color: Young adaxial between RHS 146B and RHS 146C, young abaxial between RHS 146C and RHS 146B; mature adaxial between RHS 146B and RHS 146C with slight blush of nearest RHS 187A, mature abaxial between RHS 146C and RHS 146B;

Veins: Parallel; color adaxial between RHS 146B and RHS 138A, and abaxial nearest RHS 137B;

Flower description:

Flowers: Funnelform; single, with two sets of three tepals; zygomorphic, incomplete; up to 16 per scape, mostly distally arranged on typically 4 branches; upward and outwardly facing; about 13.3 cm across and 10.8 cm tall to exserted stigma, corolla about 7.5 cm deep; individually lasting for about one day; peduncle remains effective from mid-July into early-August for approximately three weeks in Zeeland, Mich. with repeating into October;

Flower fragrance: Lightly sweet;

Buds one day prior to opening: Oblate ellipsoid with bluntly acute apex and tepals beginning to separate, and basal one-fifth narrowed terete; about 92.0 mm long and about 30.0 mm in diameter at widest point with basal one-fifth narrowing to about 11.0 mm diameter;

Bud color one day from opening: Apical 5.0 mm nearest RHS 24B, central portion nearest RHS 29C developing an undertone of nearest RHS 151B toward base, basal 15 mm between RHS 150C and RHS 150D;

Tepals: 2 sets of 3;

Inner tepals: Rounded; glabrous; rounded apex; consistently and considerably crisped margins to about 5.0 mm deep; base truncate, fused in proximal 18.0 mm; width at fusion about 10.0 mm; midrib fluted about 2.0 mm wide on abaxial surface, flat adaxial; recurved about 60 to 90 degrees in distal one-eight; about 6.0 cm across at widest point and about 10.3 cm long;

Outer tepals: Broadly lanceolate to elliptic; glabrous; rounded apex; fused in proximal 18.0 mm; irregularly and slightly crisped margin to about 4.0 mm wide, central portion of outer tepal flat; tepals reflexed about 90 degrees in distal one-fifth; about 11.0 cm long and 4.3 cm across;

Inner tepal color adaxial: Center between RHS 37A and 35C, thin margin about 0.5 mm wide of nearest RHS 162C, inside of thin margin another marginal layer about 3.0 mm thick of nearest RHS N77A, with 1.0 cm thick band nearest N77A forming a "V" pointing toward apex, proximal 10 mm of margin about 3.0 mm wide nearest RHS 19D, midrib nearest RHS 24D, region proximal eye nearest and RHS 17B, base nearest RHS 151D;

Inner tepal color abaxial: Picotee margin nearest N77A, longitudinal center nearest RHS 25D, base nearest RHS 151D;

Outer tepal color adaxial: Center between RHS 179B and 179C, thin margin less than 1.0 mm wide of nearest RHS 162B, inside of thin margin another marginal layer about 3.0 mm thick of nearest RHS N77A, with 1.0 cm thick band of between RHS N186B to N186C forming a "V" pointing toward apex, proximal margin about 3.0 mm wide between RHS 24D and RHS 23D, proximal midrib about 2.5 mm wide nearest RHS 22C, region proximal eye between RHS 16B and RHS 16C, base nearest RHS 151D;

Outer tepal color abaxial: Abaxial margin about 8 to 10 mm wide between RHS 29C and RHS 31D, longitudinal center mixture of RHS 23C, RHS 24C with blush of nearest RHS N25D, base nearest RHS 151D;

Pedicel: Cylindrical; approximately 10.0 mm long, 6.0 mm diameter at base;

Pedicel color: Nearest blend between RHS 138A and RHS 146B;

Peduncle: Usually three per plant during peak initial flowering and two per plant with repeat flowering, erect to about 70.0 cm tall and 8.0 mm diameter at base, average 65.0 cm tall; extending above foliage;

Peduncle color: Nearest blend between RHS 138A and RHS 146B;

Gynoecium: Single; tri-carpelled; glabrous; about 10.9 cm long;

*Style*.—Single, about 10.0 cm long, 2.0 mm diameter, slightly arcuate upward at distal one-fifth; color distally nearest RHS 25D, middle distally between RHS 28C and RHS 28D and proximally nearest RHS 18C.

*Stigma*.—1.0 mm to 2.0 mm in diameter; color nearest RHS 162D.

*Ovary*.—Ellipsoidal; smooth; acute apex, truncate base; about 8.0 mm long and 5.0 mm diameter at base; color between RHS 145B and RHS 145C.

Androecium: Six; glabrous;

*Filaments*.—Six; cylindrical; adnate to inner tepal in basal 18.0 mm above ovary; arcuate upward in distal 10 mm; free in distal 62.0 mm long from fusion point on tepal; 80.0 mm long; basally applanate; 4.5 mm across and 2.0 mm thick; color between RHS 25C and RHS 25B distally and base nearest RHS 17D.

*Anthers*.—Oblong; dorsifixed, longitudinal; about 10.0 mm long and 4.0 mm wide; color closest to RHS N77A.

*Pollen*.—Elliptical, less than 0.1 mm long; color nearest RHS 17A.

Fruit and seeds have not been observed;

Disease and pest resistance and tolerance: 'Hungry Eyes' has not shown resistance to diseases and pests beyond that common for daylilies, and given the northern testing regions the new plant has not been exposed to daylily rust, *Puccinia hemerocallidis*. The plant grows best and shows best coloration with plenty of moisture, adequate drainage and light shade during the hottest period of the day, but is able to tolerate some drought when mature and direct sun without leaf burn when provided sufficient water.

Hardiness at least from USDA zone 3 through 9, and other disease resistance and tolerance is typical of that of other daylilies. The new plant is useful for landscaping en masse, as a single specimen or small groups.

The invention claimed is:

1. A new and distinct ornamental daylily plant cultivar named *Hemerocallis* 'Hungry Eyes' as herein described and illustrated.

* * * * *